US00PP10095P

United States Patent [19]

Henny

[11] Patent Number: Plant 10,095

[45] Date of Patent: Nov. 4, 1997

[54] MANDEVILLA: JUMBO BLUSH

[75] Inventor: Richard J. Henny, Tavares, Fla.

[73] Assignee: Gem Ornamentals, Inc., Tavares, Fla.

[21] Appl. No.: 637,121

[22] Filed: Apr. 24, 1996

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 8,479 11/1993 Henny ..... Plt./54.1
P.P. 8,842 7/1994 Henny ..... Plt./54.1

OTHER PUBLICATIONS

Bailey, L. H., et al., "Mandevilla", *Hortus Third,* MacMillan Publ. Co., Inc., N.Y. (1976) p. 711.

Graf, A. B., (Ed.), "Mandevilla", *Exotica,* Roehrs Co., Rutherford, N.J., (1967), p. 1651.

Huxley, A., et al. (Eds.), "Mandevilla", *The New Royal Horticultural Society Dictionary of Gardening* (1992), vol. 3, p. 187.

*Primary Examiner*—James R. Feyrer
*Attorney, Agent, or Firm*—Godfrey & Kahn, S.C.

[57] ABSTRACT

A new and distinct variety of Mandevilla characterized by large funnelform to trumpet-shaped flowers that open pale pink, fade to white within one to three days after anthesis and remain on the plant an additional two to three days. Flower color is highlighted by a bright red-purple throat that becomes somewhat lighter as the flower ages.

1 Drawing Sheet

BACKGROUND INFORMATION

The present invention relates to a new and distinct hybrid of Mandevilla that originated from self-pollination of Mandevilla×'Alice Du Pont', a member of the family Apocynaceae. The parent is believed to be an interspecific hybrid; the seed parent of which was *Mandevilla splendens.* This new Mandervilla is the result of deliberate pollinations performed by the inventor in a greenhouse at Gem Ornamentals in Tavares, Fla. in 1990. This new variety was selected out for further evaluation because it had large, pale pink flowers with a bright red-purple throat. The flowers faded to white with age. The new variety has been reproduced by asexual propagation (cuttings) at the same location. Each of the progeny exhibits identical characteristics to the original mother plant establishing this hybrid as reproducible and true to type.

This new hybrid is unlike any Mandevilla commercially available nor like any of those described by Graf or Bailey (see references) as evidenced by the following unique combinations of characteristics.

1. Large funnelform to trumpet-shaped flowers that open pale pink, fade to white within one to three days after anthesis and remain on the plant an additional two to three days.

2. Flower color is highlighted by a bright red-purple throat that becomes somewhat lighter as the flower ages.

3. Elliptic-ovate shaped, leathery, shiny dark green and evergreen leaves.

DESCRIPTION OF THE DRAWING

This new variety of Mandevilla is illustrated by the accompanying photographic drawing.

DETAILED PLANT DESCRIPTION

Figure 1:
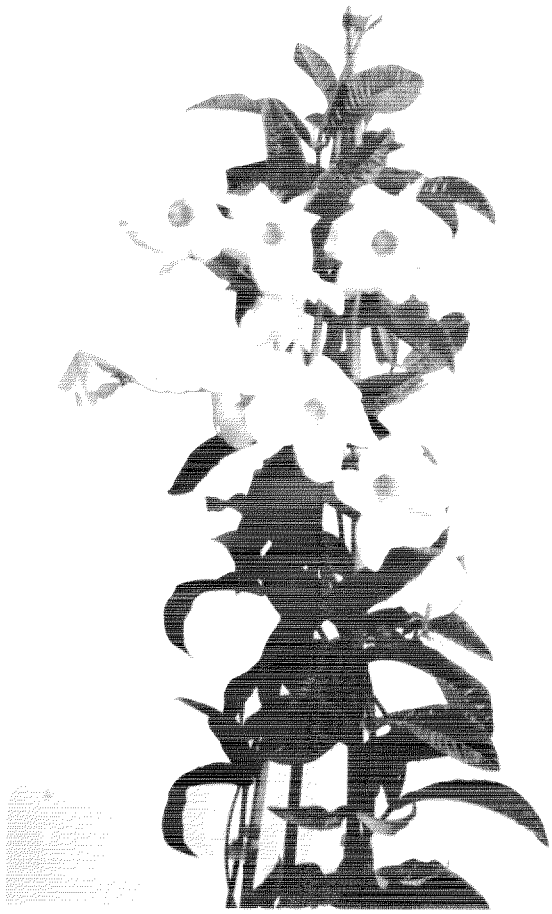
FIG. 1 is a photographic print in full color of a six-month old plant illustrating its trumpet-shaped, pale-pink to white flowers with red-purple throats.

The following is a detailed description of the new Mandevilla plant based on observations made at the nursery of Gem Ornamentals, Inc. in Lake County, Tavares, Fla. The color determinations and comparisons are all based on The R.H.S. Colour Chart published by The Royal Horticultural Society of England in association with the Flower Council of Holland. Colors are approximate as color depends on horticultural practices such as temperature, light level and fertilization rate, among others.

Growth habit: The growth habit is a woody, counterclockwise twining vine with fleshy bidentate to tetradentate (2–4 toothed) nodal appendages; opposite, elliptic to obovate leaves, and large funnelform light pink flowers borne on alternate, axillary racemes.

Stems: Stems terete, olive green (Yellow Green Group 144A to B) turning brown in age (new growth often tinged with reddish-brown), minutely tomentose, hairs initially colorless, brownish in age.

Foliage:

*Type.*—Evergreen, herbaceous.

*Leaf arrangement.*—Opposite.

*Shape.*—Elliptic to obovate, rarely ovate in small leaves.

*Length.*—(7.8) 12–18 cm.

*Width.*—(3.4) 4.5–6.9 cm.

*Apex.*—Acuminate.

*Base.*—Cordate.

*Margin.*—Entire.

*Texture.*—Leathery, rugose (tissue between lateral veins raised).

*Pubescence.*—Minutely tomentose throughout, hairs colorless, erect.

*Petiole.*—Channeled adaxially, minutely tomentose, 0.5–1.0 cm long.

*Color.*—Upper leaf surface glittering Yellow-Green Group 139A to 135A; midrib and lateral veins dull Yellow-Green Group 143C. Lower leaf surface opaque Yellow-Green Group 147B. Midrib below Yellow-Green Group 145D.

Inflorescence:

*Type.*—Simple raceme, apparently indeterminate.

*Position.*—Lateral, axillary, one per node.

*Peduncle.*—5.5–11.6 cm long, minutely papillose.

*Bracts.*—Narrowly triangular, herbaceous, 0.5–1.0 cm long, 0.2–0.4 cm wide.

*Pedicel.*—Twisted, minutely papillose, 1.3–1.8 cm long.

*Color.*—Peduncle and rachis of inflorescence — R.H.S. Fan 3 Yellow Green Group 144A and 144B. Bract-R.H.S. Fan 3 Yellow Green Group 144B with tip and apical margins R.H.S. Red-Purple Group 60A. Pedicel — R.H.S. Fan 3 Yellow Green Group 144B remaining yellow green until the flower falls.

*Number of flowers.*—8 to 9 (or more) produced per raceme, alternate but occasionally subopposite. One to three flowers per raceme are open at one time.

*Inflorescence length.*—10–30 cm (or more) long, longer than subtending leaves, increasing with age.

Flowers produced throughout the flowering season of March to November at Tavares, Fla.

Flowers:

*Structure.*—Bisexual, calyx of 5 basally connate sepals, corolla of five parts, sympetalous, basal portion a straight tube proper the corolla widening above into a campanulate throat and spreading corolla lobes, stamens epipetalous, filaments bearded, anthers connivent, bilobed at base, adhering to stigma.

*Calyx lobes.*—Ovate, accuminate at tip, thickened medially and at base, minutely papillose.

*Corolla tube.*—Straight, minutely papillose, 1.5–1.8 cm long, 0.4–0.5 cm in diameter at base.

*Corolla throat.*—Bell-shaped, 3.4–3.6 cm long, 2.5–3.0 cm wide at the opening.

*Corolla width.*—12.0–14.5 cm.

*Corolla lobes.*—Very strongly unequal sided (dimitate), apex obtuse, slightly excentric, broadly spatulate-elliptic to obovate. The left hand side greatly reduced ½ ovate, the right hand side broadly elliptic to broadly ovate; glabrous.

*Fragrance.*—The light scent of petunia is noticeable in the morning, being most pronounced at mid-day and fading later in the afternoon.

*Color.*—At opening, the outer surface of the tube proper is light green (R.H.S. Fan 3 Yellow Green Group 145B) to cream-green (R.H.S. Fan 3 Yellow Green Group 145D). The throat is pink (R.H.S. Fan 2 Red-Purple Group 65D). Along the inner surface of the throat, the basal ¼ is yellow-green (R.H.S. Fan 3 Yellow Green Group 150B) and the apical ¾ of the throat is dark pink (R.H.S. Fan 2 Red-Purple Group 64C), darker over the venation. The outer surface of the corolla lobes are pink (R.H.S. Fan 2 Red-Purple Group 65B to 65D) toward the center, darkening at the apex to dark pink (R.H.S. Fan 2 Red-Purple Group 64C).

The inner surface of the corolla lobes are pink (R.H.S. Fan 2 Red-Purple Group 65C) darkening at the apex to dark pink (R.H.S. Fan 2 Red-Purple Group 64C). A broad triangular region of dark pink (R.H.S. Fan 2 Red-Purple Group 64C) extends about 1.0 cm up the lobe.

As the flower matures, the outer surfaces of the throat and corolla lobe fade to pale pink (paler than R.H.S. Fan 2 Red-Purple Group 62D). On the inside surface, the center of the petal lobe becomes white (R.H.S. Fan 4 White Group 155C). The deep pink (R.H.S. Fan 2 Red-Purple Group 64C) fades from the base of the petal lobe and persists only in the inner throat. The yellow-green color (R.H.S. Fan 3 Yellow-Green Group 150B) is absent in the throat of a mature flower. The broad trianglar region of dark pink (R.H.S. Fan 2 Red-Purple Group 64C) extending about 1.0 cm up the lobe fades to pale pink (R.H.S. Fan 2 Red-Purple Group 65C) the same as the petal surface.

Overall size and growth habit:

*Size.*—The ultimate size of the new variety is unknown as no plant has reached full maturity. This new hybrid has grown between 1.0 to 1.5 m in 2 months under greenhouse conditions in the summer in Tavares, Fla.

*Hardiness.*—The new variety has tolerated temperatures to 35° F. but is killed at 32° F.

*Fertility.*—The new variety is both male and female fertile.

Additional comments:

*Differences from Mandevilla×'Alice du Pont'.*—Mandevilla 'Alice du Pont' has flowers that open light pink and become very dark pink with age. In contrast, flowers of the new variety open light pink and fade to white. Average corolla width of the new variety (12–14 cm) is wider than 'Alice du Pont' (9.5–11.5 cm).

*Differences from Mandevilla 'White Delite'.*—Mandevilla 'White Delite' has smaller flowers than the new variety. The corolla width of 'White Delite' is 8–10 cm thus narrower than the new variety corolla width of 12–14 cm. The new variety has a very prominent red-purple coloration in the throat. Mandevilla 'White Delite' lacks any red-purple coloration in the throat.

REFERENCES

Bailey, L.H. and E.Z. Bailey, 1976, *Hortus Third,* MacMillian, New York.

Graf, A.B., 1978, Tropica—Color Cyclopedia of Exotic Plants and Trees, Roehrs Co., East Rutherford, N.J.

I claim:

1. A new and distinct variety of Mandevilla plant substantially as shown and described, characterized by:

a) large funnelform to trumpet-shaped flowers that open pale pink, fade to white within one to three days after anthesis and remain on the plant an additional two to three days;

b) a flower color highlighted by a bright red-purple throat that becomes somewhat lighter as the flower ages; and c) elliptic-ovate shaped, leathery, shiny dark green and evergreen leaves.

* * * * *